(12) United States Patent
Rast et al.

(10) Patent No.: US 6,649,762 B1
(45) Date of Patent: Nov. 18, 2003

(54) CRYSTAL MODIFICATION C OF 8-CYANO-1-CYCLOPROPYL-7-(1S,6S-2,8-DIAZABICYCLO-[4.3.0]NONAN-8-YL)-6-FLUORO-1,4-DIHYRO-4-OXO-3-QUINOLINE CARBOXYLIC

(75) Inventors: Hubert Rast, Leverkusen (DE); Thomas Himmler, Odenthal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/914,090

(22) PCT Filed: Feb. 14, 2000

(86) PCT No.: PCT/EP00/01202

§ 371 (c)(1),
(2), (4) Date: Aug. 22, 2001

(87) PCT Pub. No.: WO00/52009

PCT Pub. Date: Sep. 8, 2000

(30) Foreign Application Priority Data

Feb. 26, 1999 (DE) .......................... 199 08 449

(51) Int. Cl.$^7$ .................... C07D 515/02; C07D 215/16; A61K 31/44

(52) U.S. Cl. .................... 546/156; 546/113; 514/300; 514/312

(58) Field of Search .................... 514/312, 300; 546/113, 156

(56) References Cited

U.S. PATENT DOCUMENTS 6,278,013 B1 * 8/2001 Bartel

FOREIGN PATENT DOCUMENTS

| DE | 195 46 249 | 6/1997 |
|---|---|---|
| WO | 96/16055 | 5/1996 |
| WO | 97/31001 | 8/1997 |
| WO | 00/31075 | 6/2000 |
| WO | 00/31076 | 6/2000 |
| WO | 00/52010 | 9/2000 |

OTHER PUBLICATIONS

Database WPI, Section Ch, Week 298945, Derwent Publications Ltd., London, GB Class B02, AN 1989–327670, XP002139340 & JP 01 242582 A(Hokuriku Pharm Co. Ltd.), Sep. 27, 1989.

* cited by examiner

Primary Examiner—D. Margaret Seaman
(74) Attorney, Agent, or Firm—Susan M. Pellegrino

(57) ABSTRACT

The present invention relates to a defined crystal modification of 8-cyano-1-cyclopropyl-7-(1S,6S-2,8-diazabicyclo[4.3.0]nonan-8-yl)-6-fluoro-1,4-dihydro-4-oxo-3-quinolinecarboxylic acid of the formula (1), to processes for its preparation and to its use in pharmaceutical preparations.

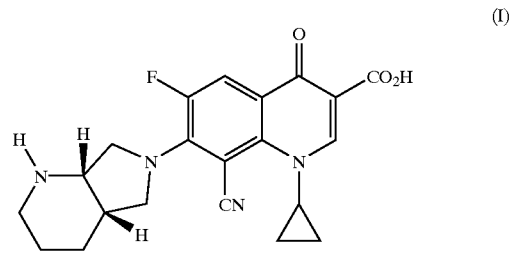

(I)

The crystal modification can be distinguished from other crystal modifications of 8-cyano-1-cyclopropyl-7-(1S,6S-2,8-diazabicyclo[4.3.0]nonan-8-yl)-6-fluoro-1,4-dihydro-4-oxo-3-quinolinecarboxylic acid of the formula (1) by its characteristic X-ray powder diffractogram and its differential thermodiagram (see description).

4 Claims, 7 Drawing Sheets

CRYSTAL MODIFICATION C OF 8-CYANO-1-CYCLOPROPYL-7-(1S,6S-2,8-DIAZABICYCLO-[4.3.0]NONAN-8-YL)-6-FLUORO-1,4-DIHYRO-4-OXO-3-QUINOLINE CARBOXYLIC

The present invention relates to a defined crystal modification of 8-cyanol-cyclopropyl-7-(1S,6S-2,8-diazabicyclo[4.3.0]nonan-8-yl)-6-fluoro-1,4-dihydro-4-oxo-3-quinolinecarboxylic acid, to processes for its preparation and to its use in pharmaceutical preparations.

Hereinbelow, 8-cyano-1-cyclopropyl-7-(1S,6S-2,8-diazabicyclo[4.3.0]nonan-8-yl)-6-fluoro-1,4-dihydro-4-oxo-3-quinolinecarboxylic acid of the formula (I) is referred to as CCDC.

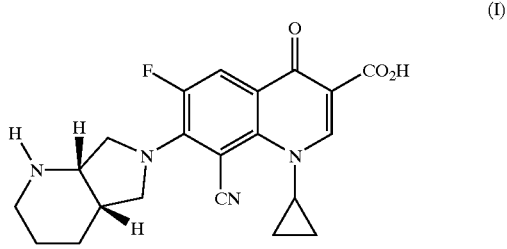

(I)

CCDC is known from DE-A 19 633 805 or PCT Appl. No. 97 903 260.4. Accordingi to these publications, it is prepared by reacting 7-chloro-8-cyano-1-cyclopropyl-6-fluoro-1,4-dihydro-4-oxo-3-quinolinecarboxylic acid with (1S,6S)-2,8-diaza-8bicyclo[4.3.0]nomane in a mixture of dimethylfornamide and acetonitrile in the presence of an auxiliary base. Water is added to the mixture and CCDC is then extracted from water using dichloromethane and is isolated by removing the extractant. This gives a powder whose crystal modification is not unambiguous. On the contrary, the powder is largely amorphous and can contain mixtures of different crystal modifications. If, by chance, a uniform crystal modification is formed, it is not clear how it can be extracted and obtained in a defined form. However, it is the precondition for preparing medicaments that, for an active compound which can be present in different crystal modifications, it can be stated unamibiguously which of its crystal modifications is used for preparing the medicament.

The partially amorphous powder which is obtained by the preparation process outlined above is furthermore hygroscopic. Amorphous solids, and in particular hygroscopic solids, are difficult to handle when being processed pharmaceutically since, for example, they may have low bulk densities and unsatisfactory flow properties. Moreover, the handling of hygroscopic solids requires special work techniques and apparatuses to obtain reproducible results, for example with respect to the active compound content or the stability of the solid formulations produced.

It is therefore an object of the invention to prepare a crystalline form of a defined modification of CCDC which, owing to its physical properties, in particular its crystal properties, is easy to handle in pharmaceutical formulations.

This object is achieved according to the invention by a novel crystalline fomi of CCDC which is referred to as modification C hereinbelow.

The invention accordingly provides the crystalline modification C of CCDC which is characterized in that it has an X-ray powder diffractogram with the reflection signals (2 theta) of high and medium intensity (>15% relative intensity) listed in Table 1 below.

BRIEF DESCRIPTION OF DRAWINGS

A characteristic X-ray powder diffractogram of the modification D of CCDC is shown in FIG. 1.

A characteristic differential thermodiagram CCDC of the modification D is shown in FIG. 2.

Figure 3:
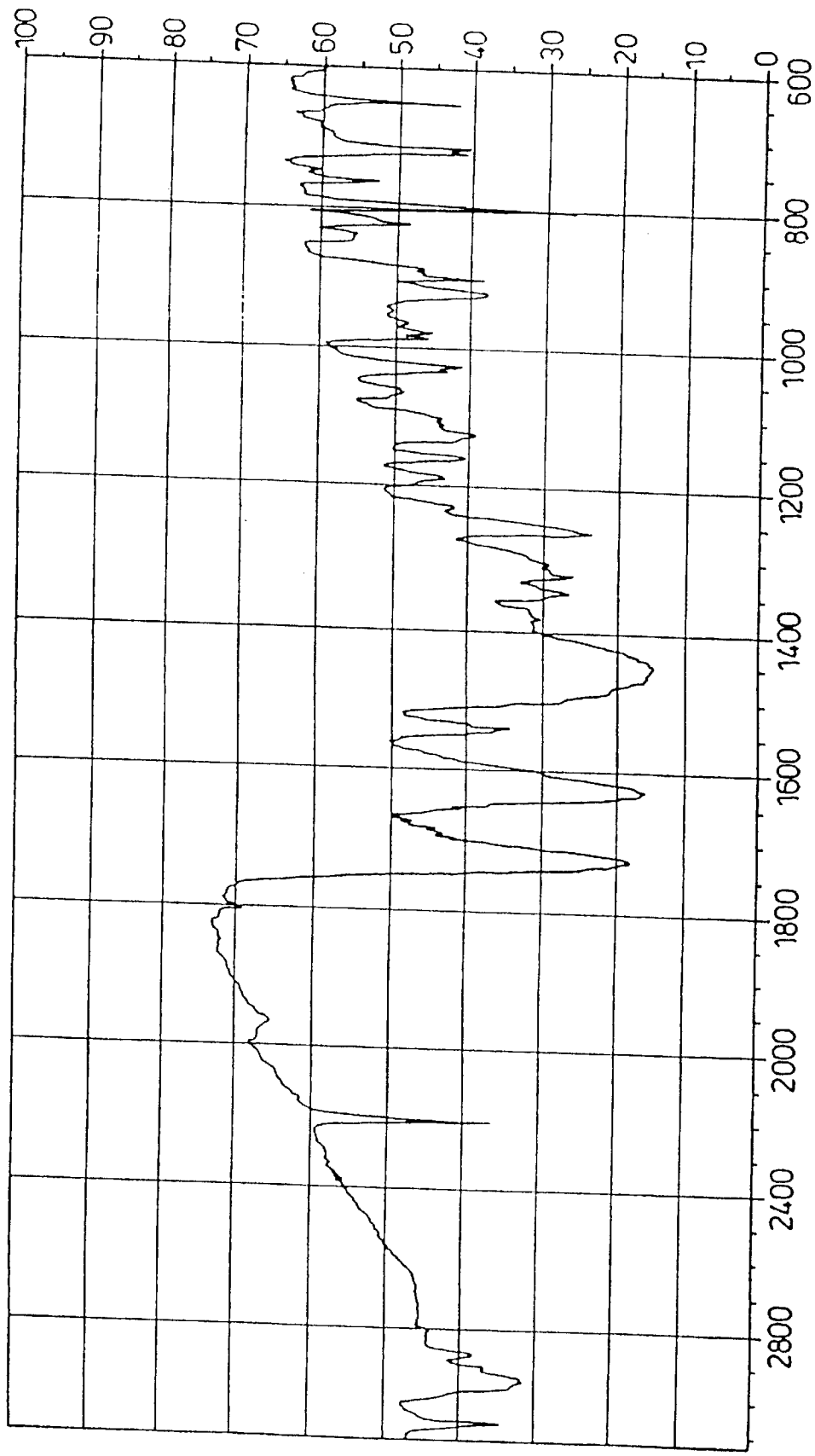

An infrared spectrum of CCDC of the modification D, measured in KBr, is shown in FIG. 3.

Figure 4:
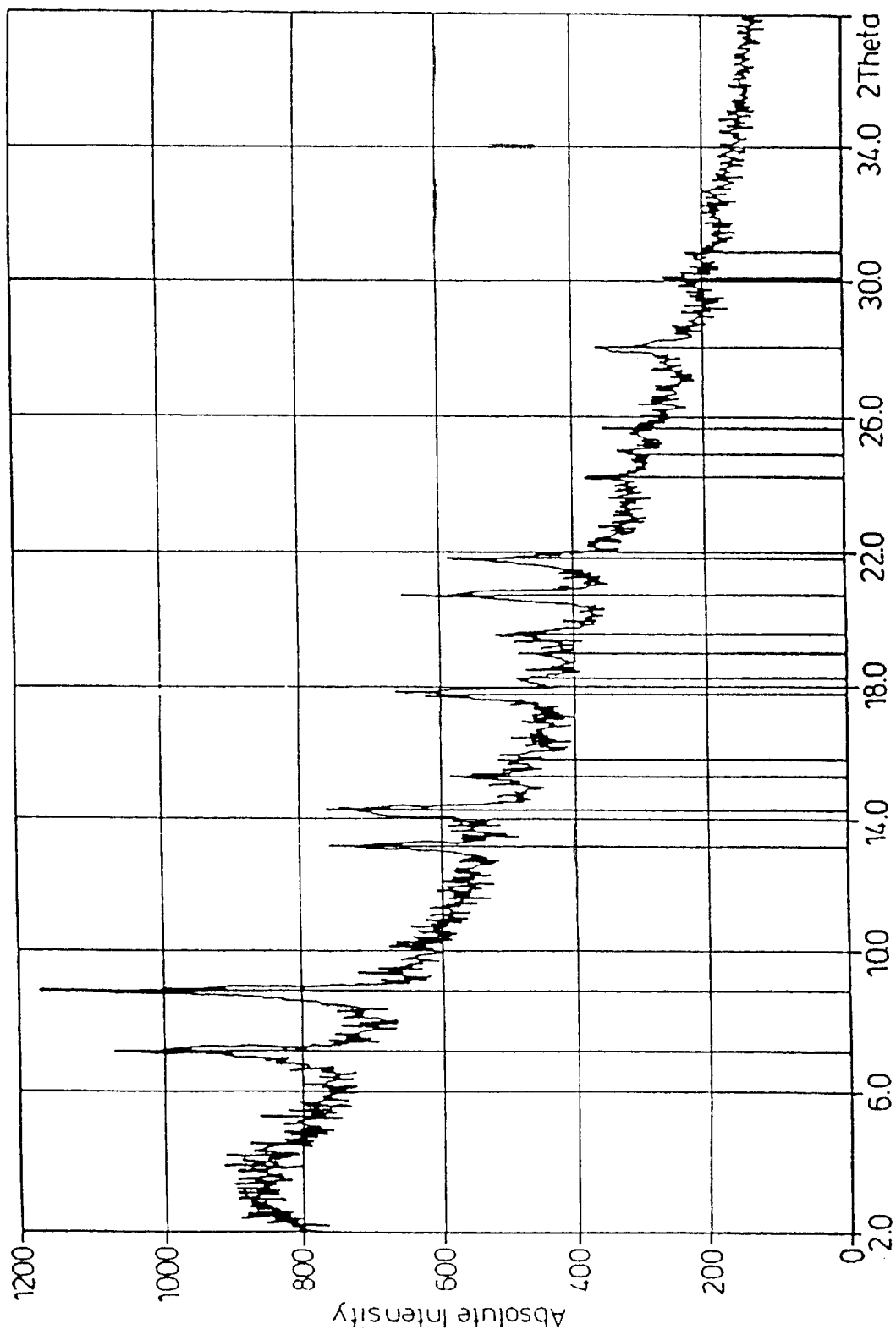

An x-ray powder diffractogram of the CCDC obtained by the comparative example at page 5 is shown in FIG. 4.

TABLE 1

X-ray powder diffractogram of CCDC of the modification C

| $2\theta$ (2 theta) |
|---|
| 5.7 |
| 12.6 |
| 15.5 |
| 17.2 |
| 20.2 |
| 26.4 |
| 27 |

Figure 1:
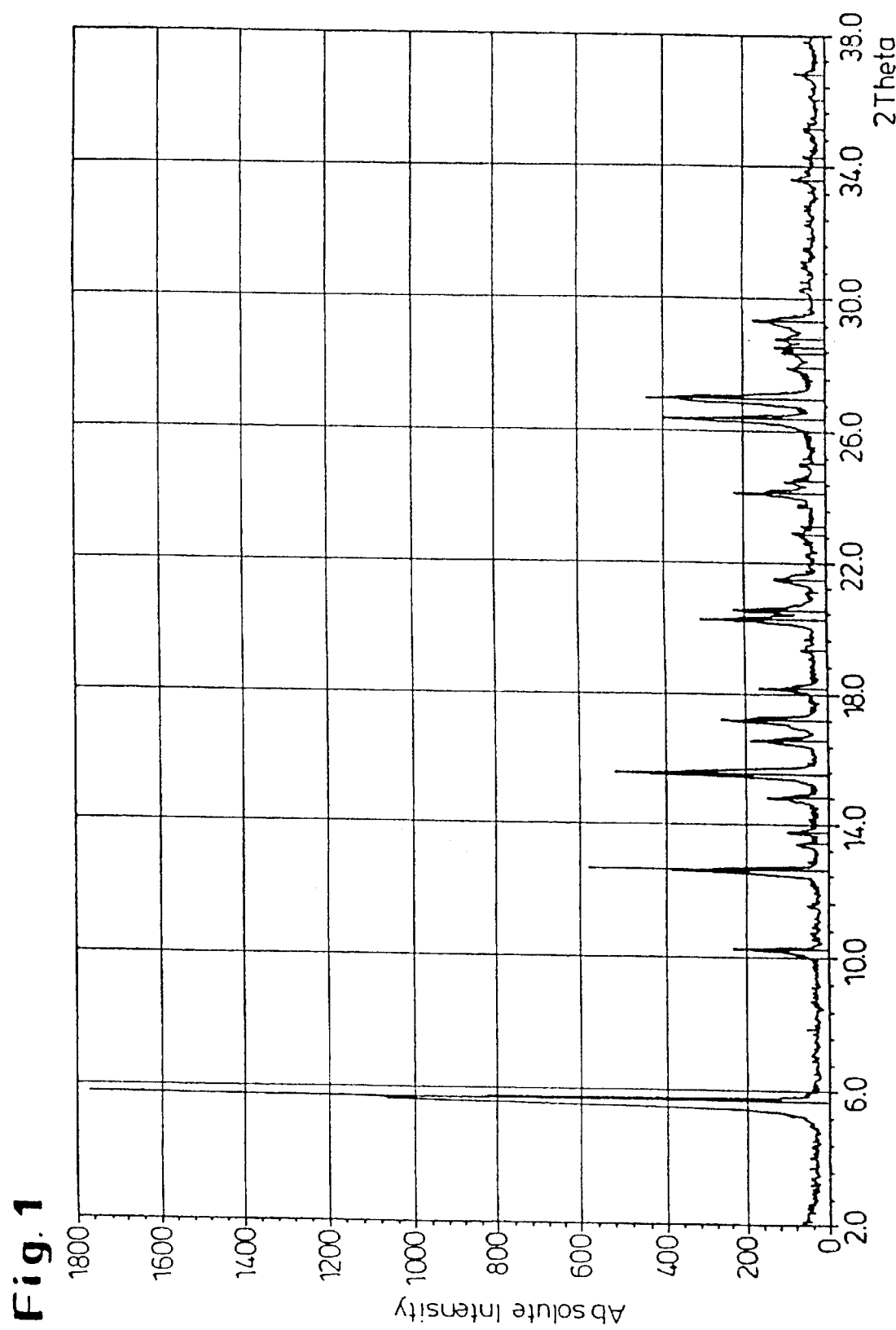

A characteristic X-ray powder diffractogram of the modification C is also shown in FIG. 1.

Moreover, the CCDC modification C according to the invention differs from other forms of CCDC in a number of further properties. These properties, on their own or together with the other parameters, may serve for characterizing the CCDC modification C according to the invention.

Figure 2:
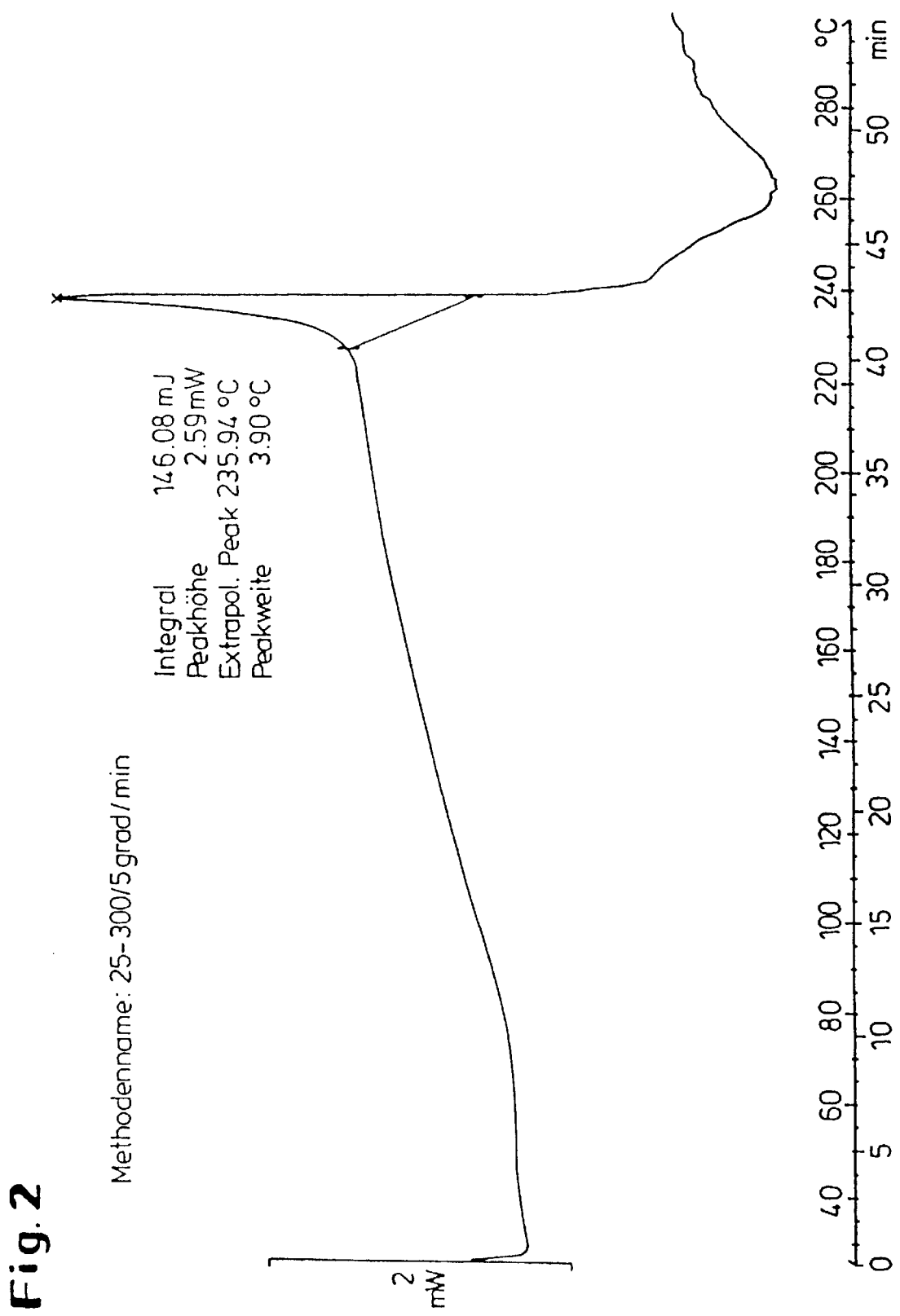

CCDC of the modification C is characterized, inter alia, by a melting point, determined with the aid of differential thermoanalysis (DTA), of from 235° C. to 237° C. A characteristic differential thermodiagram is shown in FIG. 2.

CCDC of the modification C is further characterized in that it has an infrared spectrum, measured in KBr, as shown in FIG. 3.

CCDC of the modification C is further characterized in that it is obtainable by the preparation process given below. The crystal modification C of CCDC is obtained by storing CCDC of unknown modification or amorphous CCDC at room temperature at a relative atmospheric humidity of at least 92% for a number of days until there is no more weight increase, drying the resulting water-containing product and then heating to a temperature above the rearrangement temperature.

The water-containing product can be dried by customary methods. Thus, the water-containing product can be dried, for example, at elevated temperature under reduced pressure. It is also possible to carry out the drying in the presence of a customary drying agent, such as, for example, phosphorus pentoxide.

The temperature required for converting the dried sample into modification C can be determined by DTA of the dried substance. In general the temperature is between 150° C. and 180° C.

CCDC of the crystal modification C is surprisingly stable and does not change into another crystal modification or the amorphous form, even on prolonged storage. For these reasons, it is highly suitable for preparing tablets or other solid formulations. Owing to its stability, it gives these formulations the desired long-lasting storage stability. Using the crystal modification C, it is therefore possible to prepare, in a defined and targeted manner, stable solid preparations of CCDC.

CCDC of the crystal modification C is highly active against pathogenic bacteria in the area of human or veterinary medicine. Its broad area of use corresponds to that of CCDC.

The X-ray powder diffractogram for characterizing the crystal modification C of CCDC was obtained using a transmission diffractometer STADI-P with a location-sensitive detector (PSD2) from Stoe.

The melting point of the differential thermoanalysis was obtained using the DSC 820 unit from Mettler-Toledo. Here, the sample of CCDC of the crystal modification C was heated exposed to the atmosphere in an aluminium crucible at 10 K/min.

The KBr IR spectrum was obtained using the 881 unit from Perkin-Elmer.

The examples below illustrate the invention without limiting it. The diluent/base systems described in the examples below are particularly preferred.

COMPARATIVE EXAMPLE

A mixture of 3.07 g of 7-chloro-8-cyano-1-cyclopropyl-6-fluoro-1,4-dihydro-4-oxo-3-quinolinecarboxylic acid, 1.39 g of (1S,6S)-2,8-diazabicyclo[4.3.0]nonane, 2.24 g of 1,4-diazabicyclo[2.2.2]octane (DABCO), 29.5 ml dimethylformamide and 29.5 ml of acetonitrile is stirred at room temperature for 16 hours. The reaction mixture is concentrated at a bath temperature of 60° C. using a rotary evaporator, and the residue is taken up in 10 ml of water. The resulting solution is adjusted to pH 7 using dilute hydrochloric acid, and the solid is filtered off. The filtrate is extracted three times using 20 ml of dichloromethane each time. The organic phase is dried over sodium sulphate and filtered and the filtrate is concentrated at a bath temperature of 60° C. using a rotary evaporator. This gives 2.4 g of a light-brown solid which has the X-ray powder diffractogram shown in FIG. 4 and is therefore predominantly amorphous.

Example 1

1012 g of 7-chloro-8-cyano-1-cyclopropyl-6-fluoro-1,4-dihydro-4-oxo-3-quinolinecarboxylic acid are initially charged in a mixture of 3300 ml of ethanol, 1980 ml of N-methyl-pyrrolidone and 534 g of Heünig base. The mixture is heated to reflux, and 459 g of (1S,6S)-2,8-diazabicyclo[4.3.0]nonane are then added dropwise. After the dropwise addition has ended, the mixture is stirred under reflux for another 3 hours and then allowed to cool to room temperature, and the solid is filtered off with suction and washed with a total of 1800 ml of ethanol.

Figure 5:
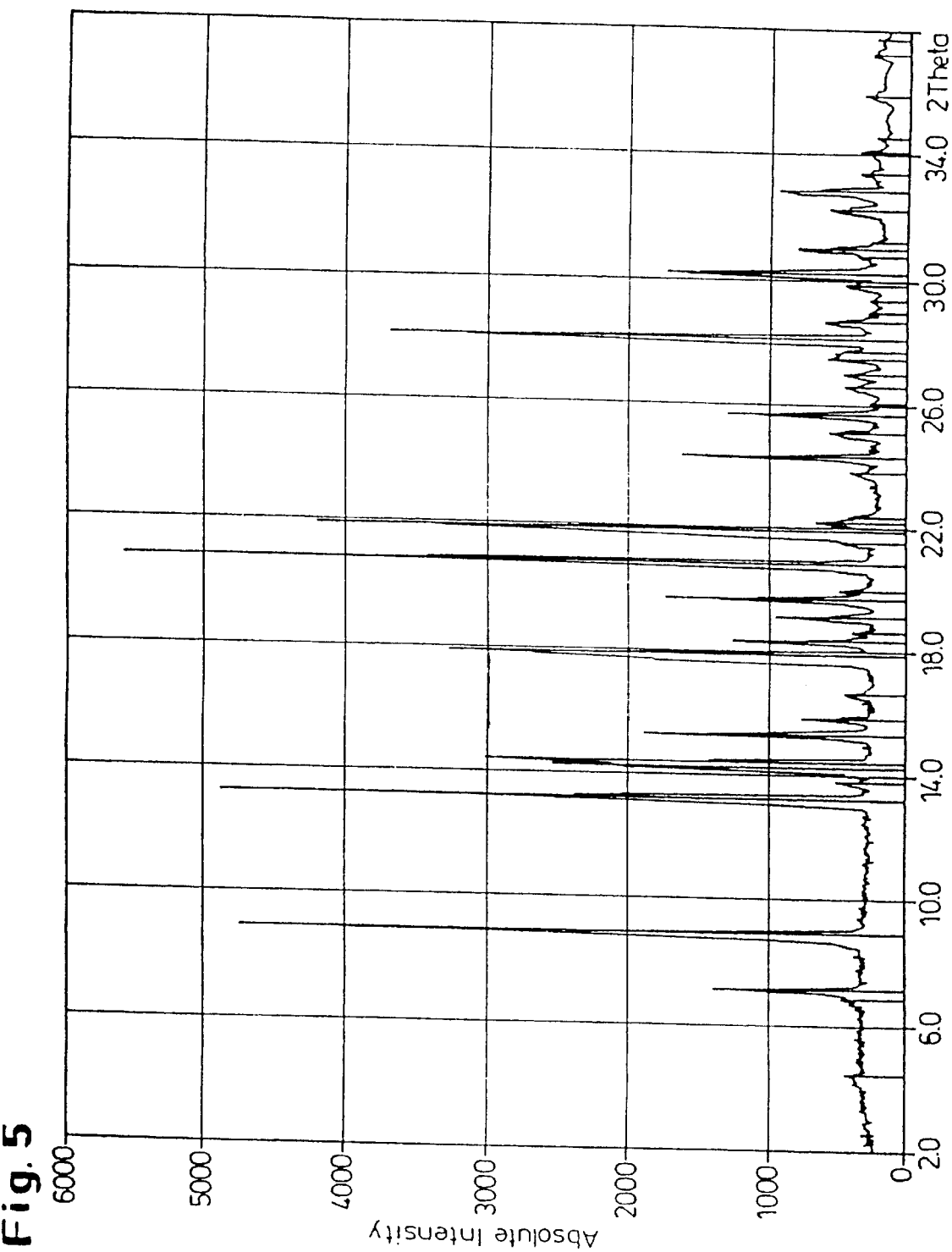

The resulting solid is suspended in a mixture of 4650 ml of ethanol and 41 g of Heünig base, and the reaction mixture is heated under reflux for 3 hours. The reaction mixture is allowed to cool again to room temperature, and the solid is filtered off with suction, washed with a total of 1000 ml of EtOH and dried at from 60 to 70° C. in a vacuum drying cabinet until the weight remains constant. This gives 1130 g of a beige solid which has the powder X-ray diffractogram shown in FIG. 5.

An amount of 500 mg of the solid prepared according to this procedure is stored at room temperature at a relative atmospheric humidity of from 95% (established using a saturated solution with sediment of $Na_2HPO_4 \times 12H_2O$ in water) for 11 days. This gives 695 mg of product.

Figure 6:
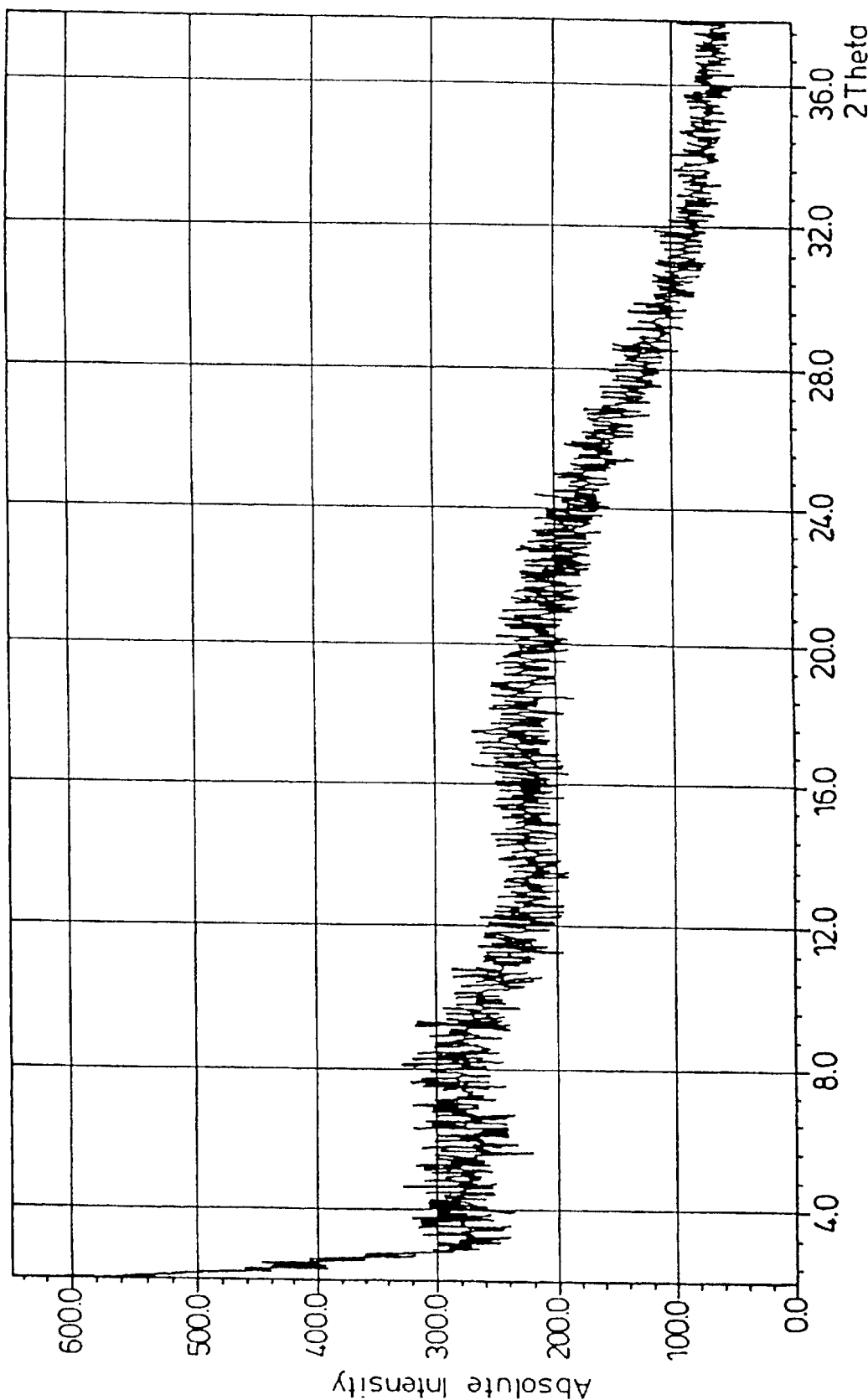
Figure 7:
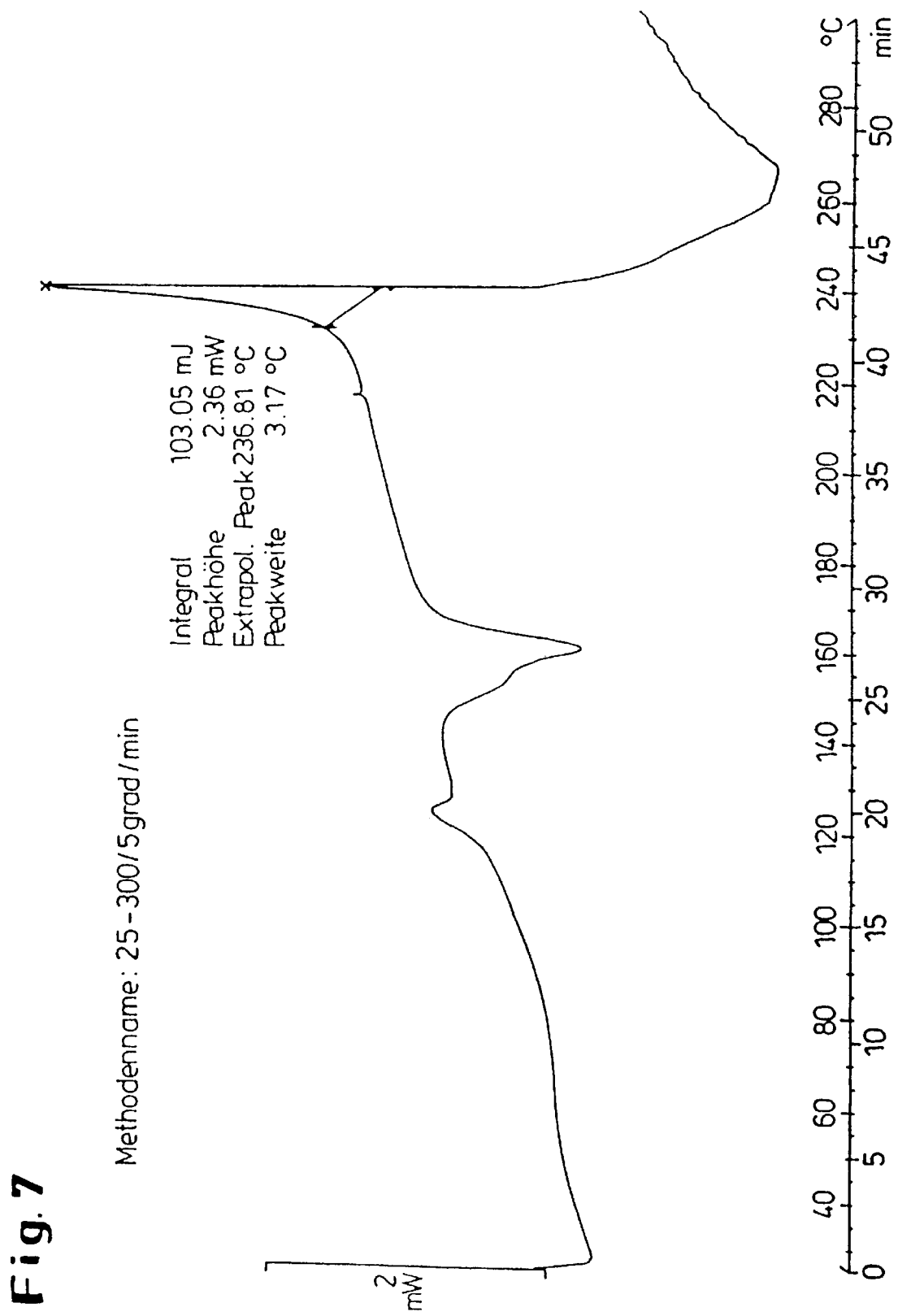

200 mg of the resulting solid are dried at 100° C. in a vacuum drying cabinet over $P_2O_5$ for 24 hours. This gives 134 mg of a solid which, according to powder X-ray diffractogram (FIG. 6), is substantially amorphous and has the DTA shown in FIG. 7.

Under nitrogen, 30 mg of the resulting solid are heated at 180° C. for 2 hours. This gives 27 mg of a solid which has the powder X-ray diffractogram shown in FIG. 1, the differential thermodiagram shown in FIG. 2 and the IR spectrum shown in FIG. 3.

What is claimed is:

1. 8-Cyano-1-cyclopropyl-7-(1S,6S-2,8-diazabicyclo[4.3.0]nonan-8-yl)-6-fluoro-1,4-dihydro-4-oxo-3-quinolinecarboxylic acid (CCDC) of the crystal modification C, characterized in that it has an X-ray powder diffractogram with the following reflection signals (2 theta) of high and medium intensity.

| 2 θ (2 theta) |
|---|
| 5.7 |
| 12.6 |
| 15.5 |
| 17.2 |
| 20.2 |
| 26.4 |
| 27. |

2. 8-Cyano-1-cyclopropyl-7-(1S,6S-2,8-diazabicyclo[4.3.0]nonan-8-yl)6-fluoro-1,4-dihydro-4-oxo-3-qinolinecarboxylic acid (CCDC) of the crystal modification C, characterized in that it has an X-ray powder diffractogram with the following reflection signals (2 theta) of high and medium intensity

| 2 θ (2 theta) |
|---|
| 5.7 |
| 12.6 |
| 15.5 |
| 17.2 |
| 20.2 |
| 26.4 |
| 27 | and a melting point, determined by DTA, of from 235° C. to 237° C.

3. A compound that is 8-Cyano-1-cyclopropyl-7-(1S,6S-2,8-diazabicyclo[4.3.0]nonan-8-yl)-6-fluoro-1,4-dihydro-4-oxo-3-quinolinecarboxylic acid (CCDC) of the crystal modification C, obtainable by exposing CCDC of unknown modification or amorphous CCDC to a relative atmospheric humidity of at least 92% until there is no further weight increase, then drying the product and subsequently heating it to a temperature above the rearrangement temperature.

4. Process for preparing CCDC of the crystal modification C, characterized in that CCDC of unknown modification or amorphous CCDC is exposed to a relative atmospheric humidity of at least 92% until there is no further weight increase, then drying the product and subsequently heating it to a temperature above the rearrangement temperature.

* * * * *